(12) United States Patent
Shimizu et al.

(10) Patent No.: US 11,672,495 B2
(45) Date of Patent: Jun. 13, 2023

(54) RADIOGRAPHIC IMAGING SYSTEM, COMPUTER READABLE STORAGE MEDIUM, OPTICAL IMAGING CONDITION SETTING METHOD, AND OPTICAL IMAGING APPARATUS

(71) Applicant: Konica Minolta, Inc., Tokyo (JP)

(72) Inventors: Amai Shimizu, Hino (JP); Takuya Yamamura, Mitaka (JP); Tatsuya Takagi, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 152 days.

(21) Appl. No.: 17/371,797

(22) Filed: Jul. 9, 2021

(65) Prior Publication Data

US 2022/0015724 A1    Jan. 20, 2022

(30) Foreign Application Priority Data

Jul. 16, 2020 (JP) .............................. JP2020-121758

(51) Int. Cl.
*A61B 6/00* (2006.01)
(52) U.S. Cl.
CPC .............. *A61B 6/40* (2013.01); *A61B 6/5205* (2013.01); *A61B 6/542* (2013.01)

(58) Field of Classification Search
CPC ....... A61B 6/4258; A61B 6/588; A61B 6/467; A61B 5/0059; A61B 5/0077; A61B 2090/365; A61B 2034/107; A61B 2090/3614; A61B 2090/3983; A61B 6/08
See application file for complete search history.

(56) References Cited

FOREIGN PATENT DOCUMENTS

| JP | H06-217973 A | 8/1994 |
|---|---|---|
| JP | 2019-033828 A | 3/2019 |
| JP | 2021194388 A | * 12/2021 |

* cited by examiner

*Primary Examiner* — Don K Wong
(74) *Attorney, Agent, or Firm* — Lucas & Mercanti, LLP

(57) ABSTRACT

A radiographic imaging system includes a radiographic imager, an optical imager and an optical imaging condition setter. The radiographic imager detects radiation emitted from a radiation source and passed through a subject to take a radiograph. The optical imager takes an optical image of a region including a region to which the radiation is emitted from the radiation source. The optical imaging condition setter sets an optical imaging condition of the optical imager based on a radiographic imaging condition for the radiograph.

11 Claims, 4 Drawing Sheets

RADIOGRAPHIC IMAGING SYSTEM, COMPUTER READABLE STORAGE MEDIUM, OPTICAL IMAGING CONDITION SETTING METHOD, AND OPTICAL IMAGING APPARATUS

CROSS-REFERENCE TO RELATED APPLICATIONS

The entire disclosure of Japanese Patent Application No. 2020-121758 filed on Jul. 16, 2020 is incorporated herein by reference in its entirety.

BACKGROUND

Technological Field

The present disclosure relates to a radiographic imaging system, a computer readable storage medium, an optical imaging condition setting method, and an optical imaging apparatus.

Description of the Related Art

There has been proposed a technology using an optical image for setting or checking imaging conditions for a radiograph(s) (radiographic imaging conditions). For example, in JP 2019-33828 A, there is disclosed a technology of determining a cassette that is used in radiographic imaging from a camera image and automatically setting the determined cassette in a console.

Further, in JPH 06-217973 A, there is disclosed disposing a TV camera that takes optical images at a conjugate position to an X-ray focal point to make a visual field of the TV camera correspond to an X-ray radiation field.

SUMMARY

Figure 4:
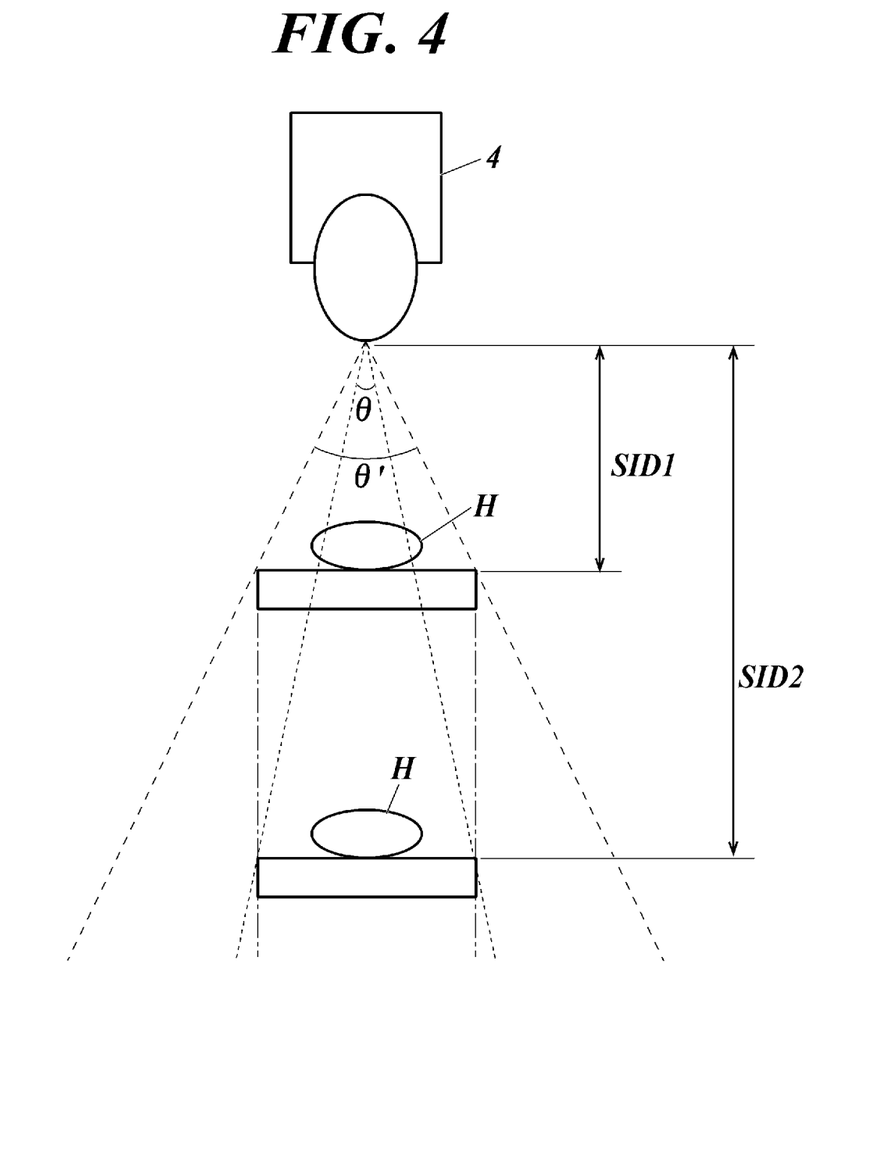
FIG. 4 schematically shows a relationship between SID and angle of view of an optical camera.

As disclosed in JP 2019-33828 A and JPH 6-217973 A, an optical camera that takes optical images is often provided near a radiation source by being integrated therewith. Hence, an area and a direction to be imaged in an optical image may change according to radiographic imaging conditions. For example, when SID (Source to Image receptor Distance), which is distance between a radiation source and a radiation detector, is changed, but the angle of view of an optical camera remains unchanged, an area of a subject to be imaged in an optical image changes from the one before SID change. For example, as shown in FIG. 4, in the case of the angle of view θ, when SID2 is changed to SID1, a narrower/smaller area of a subject H is included (imaged) in an optical image, and accordingly the subject H does not fit in the optical image. Thus, depending on radiographic imaging conditions, inconvenience occurs in checking using an optical image for radiographic imaging or analyzing an optical image for radiographic imaging.

Objects of the present disclosure include preventing inconvenience in checking using an optical image for radiographic imaging or analyzing an optical image for radiographic imaging from occurring, regardless of radiographic imaging conditions.

In order to achieve at least one of the objects, according to a first aspect of the present disclosure, there is provided a radiographic imaging system including:

a radiographic imager that detects radiation emitted from a radiation source and passed through a subject to take a radiograph;

an optical imager that takes an optical image of a region including a region to which the radiation is emitted from the radiation source; and an optical imaging condition setter that sets an optical imaging condition of the optical imager based on a radiographic imaging condition for the radiograph.

In order to achieve at least one of the objects, according to a second aspect of the present disclosure, there is provided a non-transitory computer readable storage medium storing a program that causes, of a radiographic imaging system including: a radiographic imager that detects radiation emitted from a radiation source and passed through a subject to take a radiograph; and an optical imager that takes an optical image of a region including a region to which the radiation is emitted from the radiation source, a computer to:

set an optical imaging condition of the optical imager based on a radiographic imaging condition for the radiograph.

In order to achieve at least one of the objects, according to a third aspect of the present disclosure, there is provided an optical imaging condition setting method used in a radiographic imaging system including: a radiographic imager that detects radiation emitted from a radiation source and passed through a subject to take a radiograph; and an optical imager that takes an optical image of a region including a region to which the radiation is emitted from the radiation source, the optical imaging condition setting method including:

setting an optical imaging condition of the optical imager based on a radiographic imaging condition for the radiograph.

In order to achieve at least one of the objects, according to a fourth aspect of the present disclosure, there is provided an optical imaging apparatus (i) included in a radiographic imaging system including a radiographic imager that detects radiation emitted from a radiation source and passed through a subject to take a radiograph and (ii) taking an optical image of a region including a region to which the radiation is emitted from the radiation source, the optical imaging apparatus including:

an optical imaging condition setter that sets an optical imaging condition for the optical image based on a radiographic imaging condition for the radiograph.

BRIEF DESCRIPTION OF THE DRAWINGS

The advantages and features provided by one or more embodiments of the present disclosure will become more fully understood from the detailed description given hereinbelow and the appended drawings that are given by way of illustration only, and thus are not intended as a definition of the limits of the present disclosure, wherein.

DETAILED DESCRIPTION OF EMBODIMENTS

Hereinafter, one or more embodiments of the present disclosure will be described in detail with reference to the drawings. However, the scope of the present invention is not limited to the disclosed embodiments or illustrated examples.

First Embodiment

[Configuration of Radiographic Imaging System 100]

First, configuration of a first embodiment of the present disclosure will be described.

Figure 1:
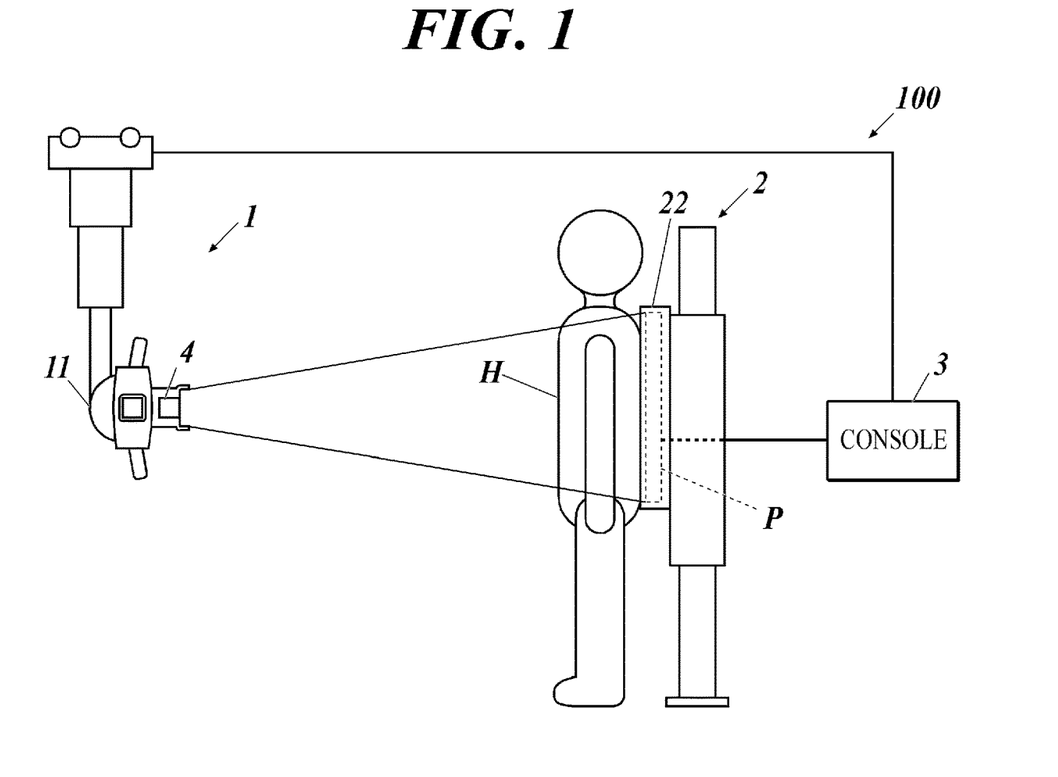
FIG. 1 shows an overall configuration of a radiographic imaging system according to an embodiment(s) of the present disclosure.

FIG. 1 shows an example of an overall configuration of a radiographic imaging system 100 according to the first embodiment of the present disclosure. The radiographic imaging system 100 is a system that images a subject H with radiation (radiographic imaging) to obtain a radiograph(s).

As shown in FIG. 1, the radiographic imaging system 100 includes a radiation emission apparatus 1, a radiation detection apparatus 2, a console 3 (optical imaging condition setter) and an optical camera 4. The console 3 is connected to the radiation emission apparatus 1, the radiation detection apparatus 2 and the optical camera 4 so as to send and receive data thereto and therefrom.

The radiation emission apparatus 1 includes a radiation source 11 disposed so as to face the radiation detection apparatus 2 with the subject H (subject) in between, and emits radiation (X-rays) to the subject H under the control of the console 3.

The radiation detection apparatus 2 is a radiographic imager that detects radiation emitted from the radiation source 11 and passed through the subject H to take a radiograph(s), and includes a detector holder 22 and a radiation detector P. The radiation detector P is configured by an FPD (Flat Panel Detector) or the like. The radiation detector P is configured such that detection elements (pixels) are arranged at predetermined points on a substrate, such as a glass substrate, in a matrix. The detection elements detect radiation (X rays) (intensity of radiation) emitted from the radiation emission apparatus 1 and passed through at least the subject H, convert the detected radiation into electric signals, and accumulate the electric signals therein. The pixels are provided with switching elements, such as TFTs (Thin Film Transistors). The radiation detector P controls the switching elements of the pixels on the basis of image reading conditions input from the console 3 to switch the pixels from which the accumulated electric signals are read, thereby reading the electric signals accumulated in the pixels and obtaining image data (frame image(s)). Then, the radiation detector P outputs the obtained image data to the console 3.

The console 3 outputs radiation emission conditions to the radiation emission apparatus 1 and also outputs the image reading conditions to the radiation detector P, thereby controlling radiation emission that is performed by the radiation emission apparatus 1 and radiograph reading that is performed by the radiation detector P. The console 3 also controls settings of the optical camera 4 and imaging (optical imaging) that is performed by the optical camera 4.

Figure 2:
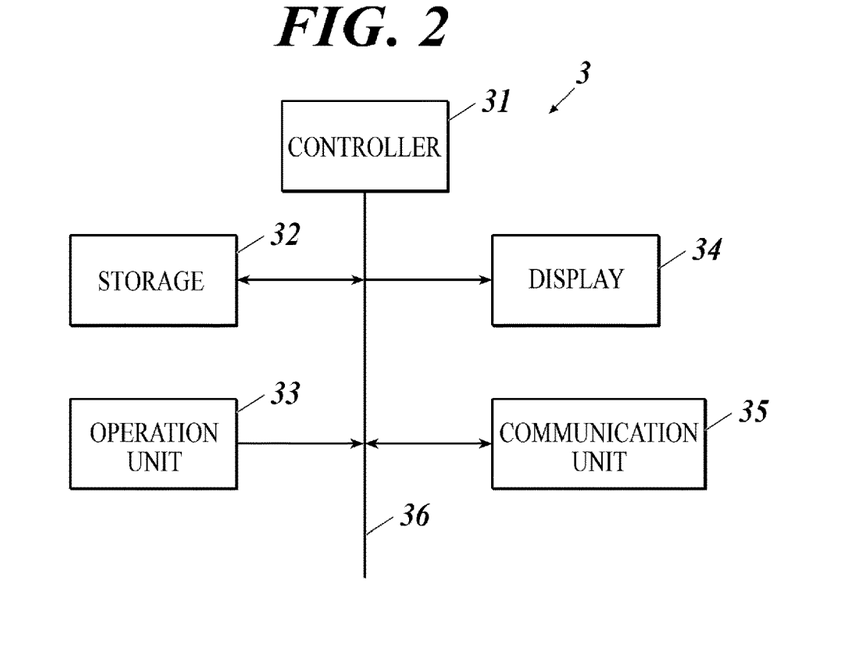
FIG. 2 is a block diagram showing a functional configuration of a console shown in FIG. 1.

The console 3 includes, as shown in FIG. 2, a controller 31, a storage 32, an operation unit 33, a display 34 and a communication unit 35. These components are connected with one another via a bus 36.

The controller 31 includes a CPU (Central Processing Unit) and a RAM (Random Access Memory). The CPU of the controller 31 reads a system program(s) and various process programs stored in the storage 32 in response to operations on/with the operation unit 33, loads the read programs into the RAM, and performs concentrated control of operation of each component of the console 3 and operation of each apparatus of the radiographic imaging system 100 in accordance with lit loaded programs.

The storage 32 is configured by a nonvolatile semiconductor memory, a hard disk and/or the like. The storage 32 stores various programs to be executed by the controller 31, parameters necessary to perform processes of the programs, data, such as process results, and so forth. The programs are stored in the form of a computer readable program code(s), and the controller 31 operates in accordance with the program code.

The storage 32 also stores each radiograph obtained by radiographic imaging in association with patient information (patient ID, patient name, etc.) and examination information (examination date, imaging conditions, etc.).

The storage 32 also stores an angle-of-view setting table and a direction setting table described below.

The operation unit 33 includes: a key board including cursor keys, number input keys and various function keys; and a pointing device, such as a mouse, and outputs, to the controller 31, instruction signals input by key operations on the keyboard or mouse operations. The operation unit 33 may have a touchscreen on the display screen of the display 34. In this case, the operation unit 33 outputs instruction signals input via the touchscreen to the controller 31. The operation unit 33 also includes an exposure switch or the like for instructing the radiation emission apparatus 1 to perform radiographic imaging.

The display 34 is configured by a monitor, such as an LCD (Liquid Crystal Display) or a CRT (Cathode Ray Tube), and displays instructions input from the operation unit 33, data and so forth in accordance with instructions of display signals input from the controller 31.

The communication unit 35 has an interface for sending and receiving data to and from the radiation emission apparatus 1, the radiation detection apparatus 2 and the optical camera 4. The console 3 may communicate with the radiation emission apparatus 1, the radiation detection apparatus 2 and the optical camera 4 by wired communication or wireless communication.

The optical camera 4 is configured by, for example, a CCD (Charge Coupled Device) camera, a CMOS (Complementary Metal Oxide Semiconductor Device) camera, an infrared camera or the like, and is an optical imager (optical imaging apparatus) that takes an optical image(s). In this embodiment, the optical camera 4 is provided for obtaining an optical image(s) of a region including a region to which radiation is emitted from the radiation source 11 (basically, a region to be irradiated with radiation or a region slightly larger than the region), and is disposed near the radiation source 11 of the radiation emission apparatus 1 by being integrated with the radiation source 11. The optical camera 4 can change its orientation (imaging direction or optical imaging direction) independently of the radiation source 11. The optical camera 4 takes an optical image in accordance with an instruction from the console 3, and sends the taken optical image to the console 3.

[Operation of Radiographic Imaging System 100]

Next, operation of the radiographic imaging system 100 will be described.

Figure 3:
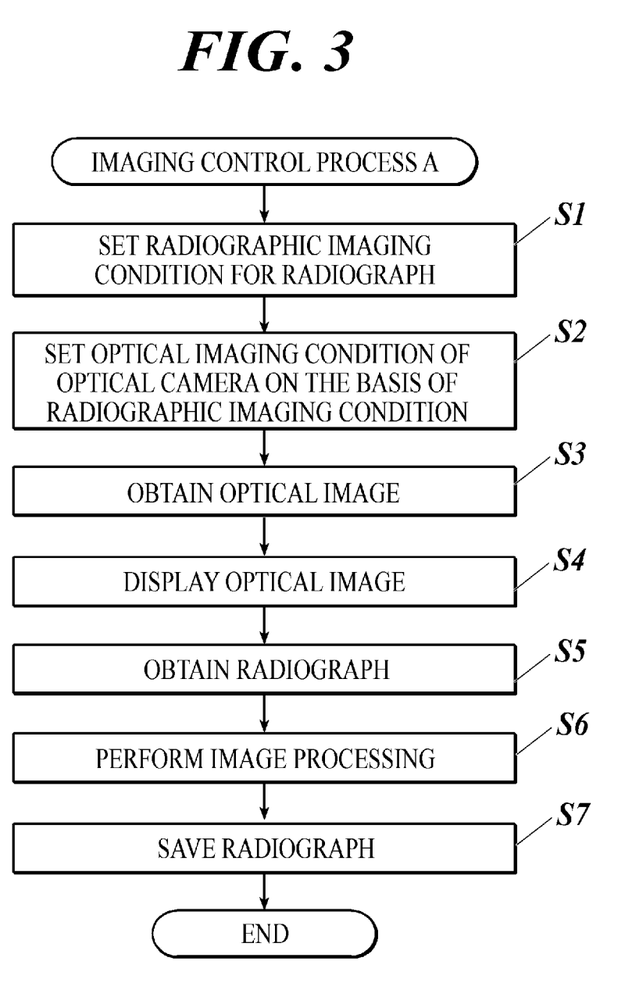
FIG. 3 is a flowchart of an imaging control process A that is performed in a first embodiment by a controller shown in FIG. 2.

FIG. 3 is a flowchart of an imaging control process A that is performed by the console 3. The imaging control process A is performed, for example, by the controller 31 and a program(s) stored in the storage 32 in cooperation with one another when patient information of the subject H and so forth are input through the operation unit 33.

First, the controller 31 sets imaging conditions for a radiograph(s) (radiographic imaging conditions) (Step S1).

For example, the controller 31 receives input of the radiographic imaging conditions through the operation unit 33, and sets the input radiographic imaging conditions to the radiation emission apparatus 1 and the radiation detector P. The radiographic imaging conditions include SID, an imaging part (site) (of a subject), an imaging direction (radiographic imaging direction), and the size of the radiation detector P that is used in radiographic imaging. The console 3 may set the radiographic imaging conditions on the basis of an imaging order from a not-shown radiology information system (RIS) or the like.

Next, the controller 31 sets imaging conditions of the optical camera 4 (optical imaging conditions) on the basis of the radiographic imaging conditions (Step S2).

In this embodiment, the optical camera 4 is for obtaining an optical image(s) of a region including a region to which radiation is emitted from the radiation source 11, the optical image being used in checking for radiographic imaging and/or being analyzed for radiographic imaging. When setting(s) of an angle of view and/or an imaging direction of the optical camera 4 (optical imaging direction) are fixed, an area and/or a direction of the subject H to be imaged in an optical image change according to the radiographic imaging conditions. This may cause inconvenience in checking (checking positioning, etc.) using an optical image for radiographic imaging and/or analyzing an optical image for radiographic imaging.

For example, when the SID is changed from SID2 to SSD1 its shown in FIG. 4, and an optical image is taken at the same angle of view θ as before although the SID becomes shorter than before, a narrower/smaller area of the subject H is included (imaged) in the optical image, and accordingly the subject H in an imaging area for a radiograph(s) (radiographic imaging area) may not fit in the optical image. Further, the area of the subject H to be imaged in a radiograph differs from one imaging part to another. When the imaging part is changed from one to another, and an optical image is taken at the same angle of view as before, an optical image of the area of the subject H suitable for the current imaging part cannot be obtained. Still further, when optical images are taken at the same angle of view in both the case where a small radiation detector P is used in radiographic imaging and the case where a large radiation detector P is used in radiographic imaging, the subject H may not fit in the optical image in the case where a small radiation detector P is used in radiographic imaging.

Further, in the case of oblique-incidence imaging, the radiation source 11 does not face the radiation detector P at right angles. When the optical camera 4 moves together with the radiation source 11 so as to face the same direction as the radiation source 11, the optical camera 4 does not face the radiation detector P at right angles, but depending on the imaging part, an optical image may be better to be taken by the optical camera 4 facing the radiation detector P at right angles. For example, in order to check an angle of OM line (orbitomeatal line) in the case of oblique-incidence imaging of the head, an optical image needs to be taken by the optical camera 4 facing the radiation detector P at right angles.

Hence, the controller 31 sets the optical imaging conditions, such as the angle of view and the imaging direction of the optical camera 4, on the basis of the radiographic imaging conditions, which include the SID, the imaging part, the radiographic imaging direction, and the size of the radiation detector P that is used in radiographic imaging.

For example, the storage 32 stores the angle-of-view setting table in which the angle of view of the optical camera 4 to be set is associated with each combination of, among the radiographic imaging conditions, the SID, the imaging part and the size of the radiation detector P that is used m radiographic imaging. This angle of view of the optical camera 4 to be set is, for example, the angle of view at which the radiographic imaging area (region to be irradiated with radiation) set for each imaging part (or for each combination of the imaging part and the size of the radiation detector P) or an area slightly larger than the radiographic imaging area is photographed (imaged), so that an optical image is obtained, and is predetermined according to the SID (i.e. is predetermined for each SID) such that the area of the subject H to be imaged in an optical image remains unchanged when the SID is changed but the imaging part and the size of the radiation detector P remain unchanged. For example, for the case shown in FIG. 4, which is the case where the SID is changed but the imaging part and the size of the radiation detector P that is used in radiographic imaging remain unchanged, the angle of view θ' and the angle of view θ are set and stored for SID1 and SID2, respectively.

The storage 32 also stores the direction setting table in which the imaging direction of the optical camera 4 to be set is associated with each combination of, among the radiographic imaging conditions, the imaging part and the radiographic imaging direction. The controller 31 refers to the angle-of-view setting table and the direction setting table, and sets the angle of view and the imaging direction of the optical camera 4 according to the set radiographic imaging conditions.

Next, the controller 31 causes the optical camera 4 to perform optical imaging, and obtains an optical image (Step S3).

For example, a photographer performs positioning of the subject H, and makes an instruction to perform optical imaging with the operation unit 33. The controller 31 causes the optical camera 4 to perform optical imaging in accordance with the optical imaging instruction made with the operation unit 33, and the optical camera 4 takes an optical image at the set angle of view in the set optical imaging direction, and sends the optical image to the console 3. Thus, the console 3 can obtain an optical image of a region including a region to which radiation is emitted from the radiation source 11; for example, a region to which radiation is emitted from the radiation source 11 or a region slightly larger than the region.

Next, the controller 31 causes live display 34 to display the optical image (Step S4).

The photographer checks (studies) the optical image and, for example, judges whether positioning is good. If the photographer judges that positioning is not good, he/she redoes the positioning. The photographer may make an instruction to redo optical imaging with the operation unit 33 so that another optical image is obtained and displayed.

Next, in response to a press of the exposure switch, the controller 31 causes the radiation emission apparatus 1 and the radiation detector P of the radiation detection apparatus 2 to perform radiographic imaging, and obtains a radiograph (Step S5).

Next, the controller 31 performs image processing on the obtained radiograph (Step S6).

As the imaging processing, at least one of the following is performed; dynamic range compression, contrast conversion, density correction, LUT (Look Up Table) processing, frequency enhancement, scatter correction, noise suppression, image trimming, image masking, image turning and image reversing.

Then, the controller 31 associates and saves (stores) the processed radiograph with the patient information and the examination information in the storage 32 (Step S7), and then ends live imaging control process A. In Step S7, the controller 31 may associate and save the optical image with the radiograph in the storage 32.

In the imaging control process A, in Step S4, the controller 31 causes live display 34 to display the optical image obtained in Step S3 for checking for radiographic imaging, but, for example, the controller 31 may analyze the optical image to determine whether a part of interest, which is preset for each imaging part, is in the radiographic imaging area. If the controller 31 determines that the part of interest is not in the radiographic imaging area, the controller 31 may warn the photographer with the display 34 or a sound. Further, the controller 31 may analyze the optical image obtained in Step S3 to obtain image processing conditions of the image processing to be performed on live radiograph.

Thus, in the first embodiment, on the basis of the set radiographic imaging conditions, the optical imaging conditions are automatically set. This can prevent inconvenience in checking positioning using an optical image or analyzing an optical image from occurring, regardless of the radiographic imaging conditions.

For example, since the angle of view of the optical camera 4 is set according to the SID such that the area of the subject H to be imaged in an optical image remains unchanged (the same) before and after SID change, it is possible to present inconvenience from occurring. For example, it is possible to prevent a situation from arising, the situation in which the subject H in the radiographic imaging area cannot fit in an optical image due to SID change.

Further, since the angle of view of the optical camera 4 is set according to the imaging part, it is possible to prevent inconvenience from occurring. For example, it is possible to prevent a situation from arising, the situation in which an optical image corresponding to the radiographic imaging area for the imaging part cannot be obtained due to imaging part change.

Still further, since the angle of view of the optical camera 4 is set according to the size of the radiation detector P, it is possible to prevent inconvenience from occurring. For example, it is possible to prevent a situation from arising, the situation in which the subject H cannot fit in an optical image due to radiation detector P change in size.

Yet further, since the optical imaging direction is set according to the radiographic imaging direction, it is possible to prevent inconvenience from occurring. For example, it is possible to prevent a situation from arising, the situation in which, in the case of oblique-incidence imaging, checking using an optical image taken by the optical camera 4 facing the radiation detector P at right angles cannot be performed.

Second Embodiment

Next, a second embodiment of the present disclosure will be described.

In the first embodiment, the optical imaging conditions (imaging conditions for an optical image(s)) are set on the basis of the set radiographic imaging conditions (imaging conditions for a radiograph(s)), but in the second embodiment, in a state in which imaging preparations are done, an optical image is taken, this obtained optical image is analyzed to determine the radiographic imaging conditions, and on the basis of the determined radiographic imaging conditions, the optical imaging conditions for an optical image that is used in checking for radiographic imaging and/or is analyzed for radiographic imaging are set.

The configuration of the radiographic imaging system 100 in the second embodiment is the same as that described in the first embodiment. Hence, description thereof is omitted, and operation of the second embodiment is described hereinafter.

In order to perform radiographic imaging, a photographer first performs imaging preparations. That is, the photographer inputs patient information and so forth with the operation unit 33 of the console 3, adjusts the orientation of the radiation source 11 and the SID, and positions the subject H. When finishing imaging preparations, the photographer makes an instruction to start imaging with the operation unit 33. When the console 3 is instructed to perform imaging through the operation unit 33, the console 3 performs an imaging control process B shown in FIG. 5. The imaging control process B is perforated by the controller 31 and a program(s) stored in the storage 32 in cooperation with one another.

Figure 5:
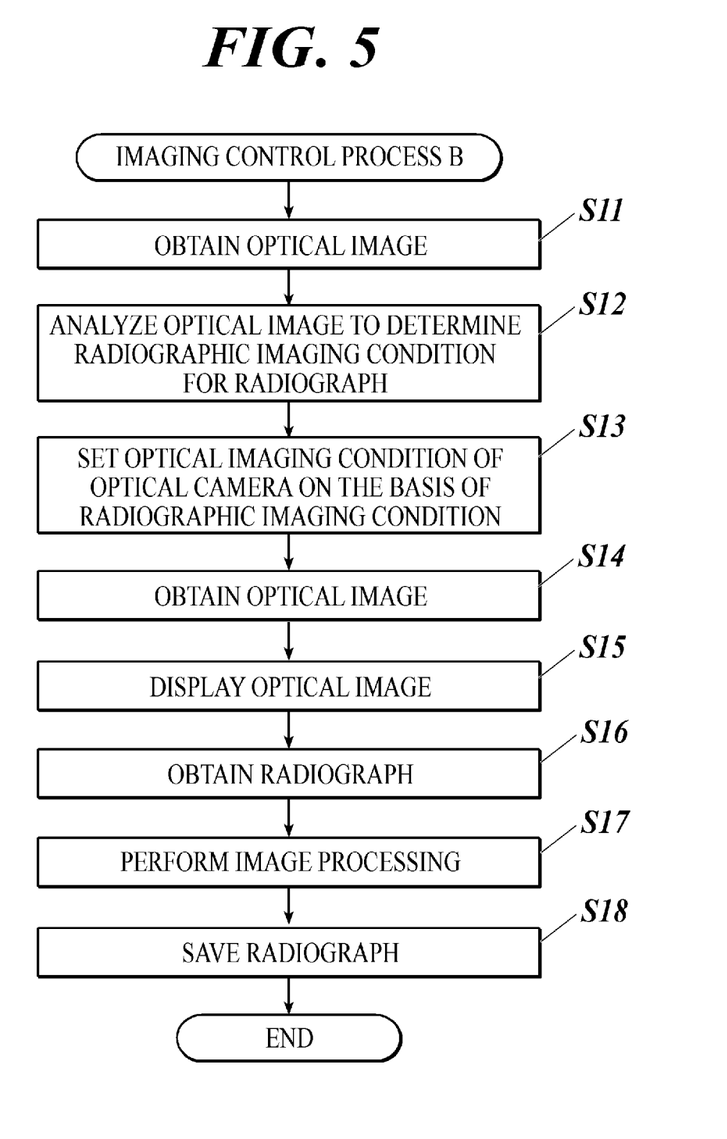
FIG. 5 is a flowchart of an imaging control process B that is performed in a second embodiment by the controller shown in FIG. 2.

First, the controller 31 causes the optical camera 4 to perform optical imaging, and obtains an optical image (Step S11).

In Step S11, the controller 31 causes the optical camera 4 to perform optical imaging in the same direction as a radiation emission direction of the radiation source 11. This makes it possible to obtain an optical image taken in the same imaging direction as that in radiographic imaging from substantially the same position as that of the radiation source 11.

Next, the controller 31 analyzes the obtained optical image to determine the radiographic imaging conditions (SID, imaging part, size of the radiation detector P, and radiographic imaging direction) (Step S12).

Methods for determining the SID, the imaging part, the radiographic imaging direction and the size of the radiation detector P from an optical image are not limited to particular methods, and hence any known methods may be used.

In order to determine the SID from an optical image, for example, a distance measurement method disclosed in "Imaging Technology Accomplishing Simultaneous Acquisition of Color Image and High-Precision Depth Map from Single Image Taken by Monocular Camera" (Toshiba Review Vol. 73 No. 1 in January 2018) by Nao MISHIMA and Takayuki SASAKI may be used.

In order to determine the imaging part and the radiographic imaging direction from an optical image, for example, a method disclosed in JP 2015-219879 A, a method using template matching or a method using machine learning may be used. The radiographic imaging direction may be determined as follows: take an optical image with the optical camera 4 in a state in which no subject is placed and from, for example, the outer shape of the detector holder 22 in the obtained optical image or the angle of size indicating lines displayed on the detector holder 22 in the obtained optical image, determine the radiographic imaging direction.

In order to determine the size of the radiation detector P, for example, a method disclosed in JP 2019-33828 A may be used.

Next, the controller 31 sets the optical imaging conditions on the basis of the radiographic imaging conditions (Step S13).

The process in Step S13 is the same as that in Step S2 shown in FIG. 3, and hence description thereof is omitted.

Next, the controller 31 causes the optical camera 4 to perform optical imaging, and obtains an optical image (Step S14).

The optical camera 4 takes an optical image at the set angle of view in the set optical imaging direction, and sends the optical image to the console 3. Thus, the console 3 can obtain an optical image of a region including a region to which radiation is emitted from the radiation source 11; for example, a region to which radiation is emitted from the radiation source 11 or a region slightly larger than the region.

Next, the controller 31 causes the display 34 to display the optical image (Step S15).

The process in Step S15 is the same as that in Step S4, and hence description thereof is omitted.

Next, in response to a press of the exposure switch, the controller 31 causes the radiation emission apparatus 1 and the radiation detection apparatus 2 to perform radiographic imaging, and obtains a radiograph (Step S16).

Next, the controller 31 performs image processing on the obtained radiograph (Step S17).

The process in Step S17 is the same as that in Step S6, and hence description thereof is omitted.

Then, the controller 31 associates and saves (stores) the processed radiograph with the patient information and the examination information in the storage 32 (Step S18), and then ends the imaging control process B. In Step S18, the controller 31 may associate and save the optical image with the radiograph in the storage 32.

In the imaging control process B, in Step S15, the controller 31 causes the display 34 to display the optical image obtained in Step S14 for checking for radiographic imaging, but, for example, the controller 31 may analyze the optical image to determine whether a part of interest, which is preset for each imaging part, is in the radiographic imaging area. If the controller 31 determines that the part of interest is not in the radiographic imaging area, the controller 31 may warn the photographer with the display 34 or a sound. Further, the controller 31 may analyze the optical image obtained in Step S14 to obtain image processing conditions of the image processing to be performed on the radiograph.

Thus, in the second embodiment, on the basis of the radiographic imaging conditions determined from an optical image, the optical imaging conditions are automatically set. This can prevent inconvenience in checking positioning using an optical image or analyzing an optical image from occurring, regardless of the radiographic imaging conditions.

For example, since the angle of view of the optical camera 4 is set according to the SID such that the area of the subject H to be imaged in an optical image remains unchanged (the same) before and after SID change, it is possible to prevent inconvenience from occurring. For example, it is possible to present a situation from arising, the situation in which the subject H in the radiographic imaging area cannot fit in an optical image due to SID change.

Further, since the angle of view of the optical camera 4 is set according to the imaging part, it is possible to prevent inconvenience from occurring. For example, it is possible to prevent a situation from arising, the situation in which an optical image corresponding to the radiographic imaging area for the imaging part cannot be obtained due to imaging part change.

Still further, since the angle of view of the optical camera 4 is set according to the size of the radiation detector P, it is possible to prevent inconvenience from occurring. For example, it is possible to prevent a situation from arising, the situation in which the subject H cannot fit in an optical image due to radiation detector P change in size.

Yet further, since the optical imaging direction is set according to the radiographic imaging direction, it is possible to prevent inconvenience from occurring. For example, it is possible to prevent a situation from arising, the situation in which, in the case of oblique-incidence imaging, checking using an optical image taken by the optical camera 4 facing the radiation detector P at right angles cannot be performed.

In the above, the first and second embodiments have been described, but the details described in the above embodiments are merely some of preferred examples of the present disclosure and not intended to limit the present invention.

For example, in the above embodiments, the angle of view of the optical camera 4 is set on the basis of the combination of the SID, the imaging part and the size of the radiation detector P for radiographic imaging. However, for example, at a screening center where only a predetermined imaging part is imaged, the angle of view of the optical camera 4 may be set on the basis of the SID and the size of the radiation detector P. Further, for example, at a facility where only a predetermined-size radiation detector P is used, the angle of view of the optical camera 4 may be set on the basis of the SID and the imaging part. Still further, for example, at a facility where only a predetermined imaging part is imaged by only a predetermined-size radiation detector P, the angle of view of the optical camera 4 may be set on the basis of the SID only.

Further, in the above embodiments, the imaging direction of the optical camera 4 (optical imaging direction) is set on the basis of the combination of the imaging part and the imaging direction (radiographic imaging direction) for radiographic imaging. However, for example, when the imaging direction for radiographic imaging can be identified from the imaging part, the imaging direction of the optical camera 4 may be set on the basis of the imaging part only.

Further, in the above embodiments, the console 3 functions as the optical imaging condition setter, but the optical camera 4 may function as the optical imaging condition setter. For example, the angle-of-view setting table and the direction setting table described above may be stored in a storage of the optical camera 4, and when receiving the radiographic imaging conditions (at least one of the SID, the imaging part, the radiographic imaging direction, and the size of the radiation detector P that is used in radiographic imaging) from the console 3, a CPU of the optical camera 4 may set the optical imaging conditions (the angle of view and/or the optical imaging direction) on the basis of the radiographic imaging conditions in cooperation with a program(s) stored in the storage of the optical camera 4. Alternatively, on the basis of an instruction from the console 3, the optical camera 4 may take, thereby obtaining, an optical image in the same direction as the radiation emission direction of the radiation source 11, analyze the obtained optical image to determine the radiographic imaging conditions, and set the optical imaging conditions (the angle of view and/or the optical imaging direction) on the basis of the determined radiographic imaging conditions.

Further, in the above, a hard disk, a nonvolatile semiconductor memory or the like is used as a computer readable medium of the programs of the present disclosure. However, this is not a limitation. As the computer readable medium, a portable storage medium, such as a CD-ROM, can also be used. Further, as a medium to provide data of the programs of the present disclosure via a communication line, a carrier wave can be used.

In addition to the above, the detailed configuration and detailed operation of each apparatus of the radiographic imaging system can also be appropriately modified within a range not departing from the scope of the present invention.

Although one or more embodiments of the present disclosure have been described and illustrated in detail, the disclosed embodiments or the like are made for purposes of not limitation but illustration and example only. The scope of the present invention should be interpreted by terms of the appended claims.

What is claimed is:

1. A radiographic imaging system comprising:
a radiographic imager that detects radiation emitted from a radiation source and passed through a subject to take a radiograph;
an optical imager that takes an optical image of a region including a region to which the radiation is emitted from the radiation source; and
an optical imaging condition setter that sets an optical imaging condition of the optical imager based on a radiographic imaging condition for the radiograph.

2. The radiographic imaging system according to claim 1, wherein the radiographic imaging condition includes at least one of a distance from the radiation source to a radiation detector of the radiographic imager, an imaging part, a radiographic imaging direction, and a size of the radiation detector.

3. The radiographic imaging system according to claim 2, wherein the optical imaging condition setter sets, as the optical imaging condition, at least one of an angle of view of the optical imager and an optical imaging direction.

4. The radiographic imaging system according to claim 3, wherein the optical imaging condition setter sets the angle of view of the optical imager according to the distance from the radiation source to the radiation detector such that an area of the subject to be imaged in the optical image remains unchanged.

5. The radiographic imaging system according to claim 2, wherein the optical imaging condition setter analyzes the optical image taken by the optical imager to determine at least one of the distance from the radiation source to the radiation detector of the radiographic imager, the imaging part, the radiographic imaging direction, and the size of the radiation detector.

6. The radiographic imaging system according to claim 5, wherein the optical imaging condition setter sets, as the optical imaging condition, an angle of view of the optical imager based on at least one of the distance from the radiation source to the radiation detector, the imaging part, and the size of the radiation detector determined.

7. The radiographic imaging system according to claim 5, wherein the optical imaging condition setter sets, as the optical imaging condition, an optical imaging direction of the optical imager based on at least one of the imaging part and the radiographic imaging direction determined.

8. The radiographic imaging system according to claim 5, wherein the optical imager is provided by being integrated with the radiation source, and
wherein the optical image that is analyzed by the optical imaging condition setter is an image taken by the optical imager in a same direction as a radiation emission direction of the radiation source.

9. A non-transitory computer readable storage medium storing a program that causes, of a radiographic imaging system including: a radiographic imager that detects radiation emitted from a radiation source and passed through a subject to take a radiograph; and an optical imager that takes an optical image of a region including a region to which the radiation is emitted from the radiation source, a computer to:
set an optical imaging condition of the optical imager based on a radiographic imaging condition for the radiograph.

10. An optical imaging condition setting method used in a radiographic imaging system including: a radiographic imager that detects radiation emitted from a radiation source and passed through a subject to take a radiograph; and an optical imager that takes an optical image of a region including a region to which the radiation is emitted from the radiation source, the optical imaging condition setting method comprising:
setting an optical imaging condition of the optical imager based on a radiographic imaging condition for the radiograph.

11. An optical imaging apparatus (i) included in a radiographic imaging system including a radiographic imager that detects radiation emitted from a radiation source and passed through a subject to take a radiograph and (ii) taking an optical image of a region including a region to which the radiation is emitted from the radiation source, the optical imaging apparatus comprising:
an optical imaging condition setter that sets an optical imaging condition for the optical image based on a radiographic imaging condition for the radiograph.

* * * * *